United States Patent [19]

Nagakura et al.

[11] 3,988,366
[45] Oct. 26, 1976

[54] 5-ACETYL-1,2,6-TRIMETHYLTRICYCLO[5,3,2,0$^{2,7}$]DODECA-5-ENE PERFUME COMPOSITION

[75] Inventors: Akira Nagakura, Kawaguchi; Susumu Akutagawa, Yohohama; Haruki Kurihara, Tokyo, all of Japan

[73] Assignee: Takasago Perfumery Co., Ltd., Tokyo, Japan

[22] Filed: Oct. 14, 1975

[21] Appl. No.: 622,354

Related U.S. Application Data

[62] Division of Ser. No. 537,002, Dec. 27, 1974.

[30] Foreign Application Priority Data

Apr. 1, 1974    Japan.............................. 49-36747

[52] U.S. Cl. ........................... 252/522; 260/568 F
[51] Int. Cl.$^2$.............................................. C11B 9/00
[58] Field of Search..................... 252/522; 260/611

[56] References Cited
UNITED STATES PATENTS 3,799,987   3/1974   Kitchens et al. ................... 252/522

*Primary Examiner*—Veronica O'Keefe
*Attorney, Agent, or Firm*—Sughrue, Rothwell, Mion, Zinn & Macpeak

[57] ABSTRACT

5-Acetyl-1,2,6-trimethyltricyclo[5,3,2,0$^{2,7}$]dodeca-5-ene having the formula (I)

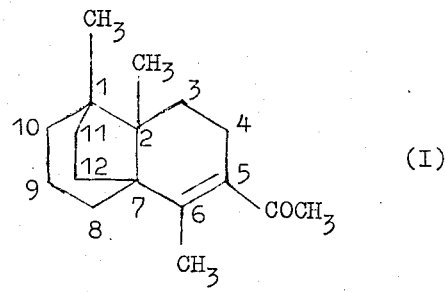

and a process for producing this compound. This compound is useful as a perfume.

1 Claim, 3 Drawing Figures

5-ACETYL-1,2,6-TRIMETHYLTRICYCLO[5,3,2,0²,⁷]DODECA-5-ENE PERFUME COMPOSITION

This is a division of application Ser. No. 537,002, filed Dec. 27, 1974.

BACKGROUND OF THE INVENTION

1. Field of the Invention

This invention relates to 5-acetyl-1,2,6-trimethyltricyclo[5,3,2,0$^{2,7}$]dodeca-5-ene and to a process for producing this compound.

2. Description of the Prior Art

Amber-like fragrant substances are important starting materials for a blended perfume, and, of these substances, ambergris obtainable from sperm whales is the most expensive. The fragrance component of this ambergris was clarified by E. Lederer and L. Ruzicka in 1946 to be a substance formed from ambrein which is a triterpenic compound. Ever since, many attempts to synthesize amber-like fragrant substances equal to the natural material, or similar substances have been made. Some of them can be utilized as a substitute for expensive ambergris. For example, manool derivatives, which are diterpenic compounds and can be obtained from a special needle-leaf tree, are widely used as such a substitute. However, in general, the amber-like fragrant substances are difficult to synthesize and moreover, special natural products are required as a starting material to synthesize amber-like fragrant substances. Therefore, synthetic amber-like fragrant substances are inevitably expensive.

SUMMARY OF THE INVENTION

This invention provides 5-acetyl-1,2,6-trimethyltricyclo[5,3,2,0$^{2,7}$]dodeca-5-ene having the formula (I)

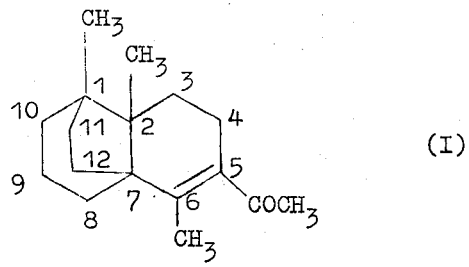

(I)

which has an excellent wood-like or amber-like fragrance, and a process for producing 5-acetyl-1,2,6-trimethyltricyclo[5,3,2,0$^{2,7}$]dodeca-5-ene (hereinafter "Compound (I)") comprising acetylating 1,2,6-trimethyltricyclo[5,3,2,0$^{2,7}$]dodeca-5-ene (hereinafter "Compound (II)") in the presence of an acid catalyst.

BRIEF DESCRIPTION OF THE ACCOMPANYING DRAWINGS

DETAILED DESCRIPTION OF THE INVENTION

Figure 1:
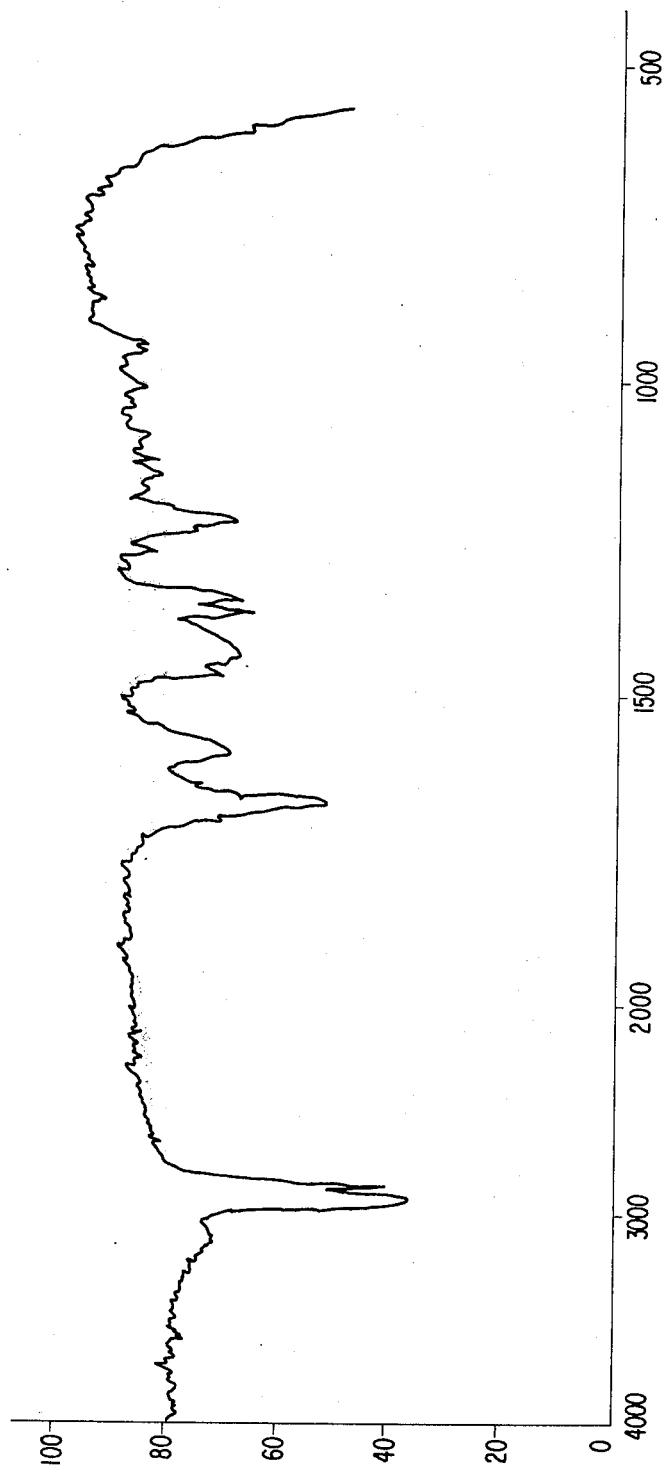
FIG. 1 is an infrared spectrum of Compound (I) obtained according to the present invention.
Figure 2:
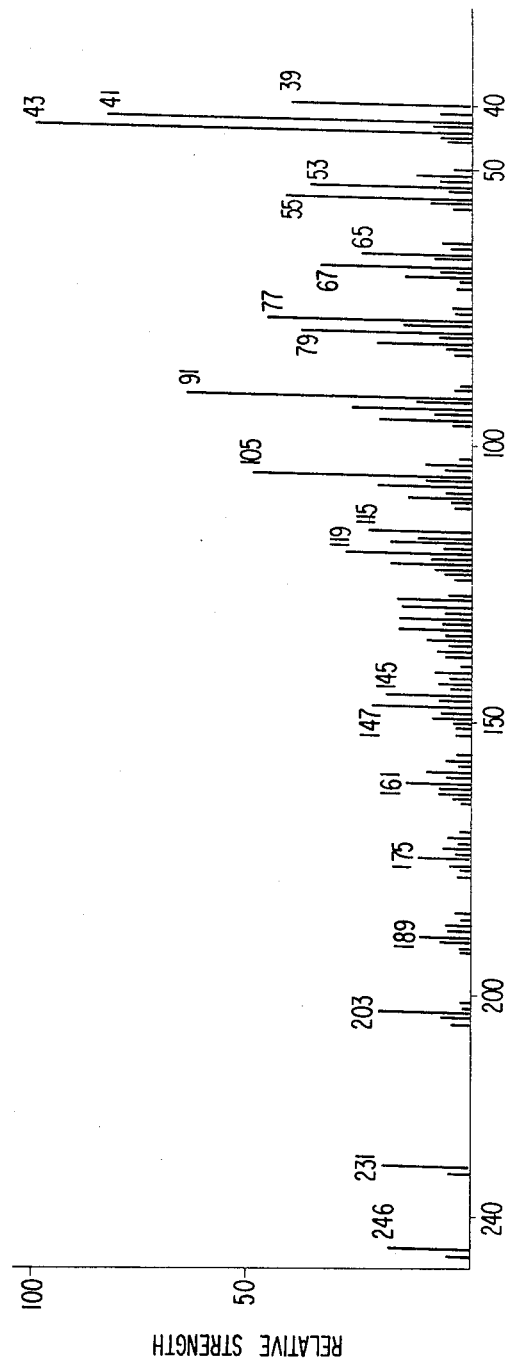
FIG. 2 is a mass spectrum of Compound (I) obtained according to the present invention.
Figure 3:
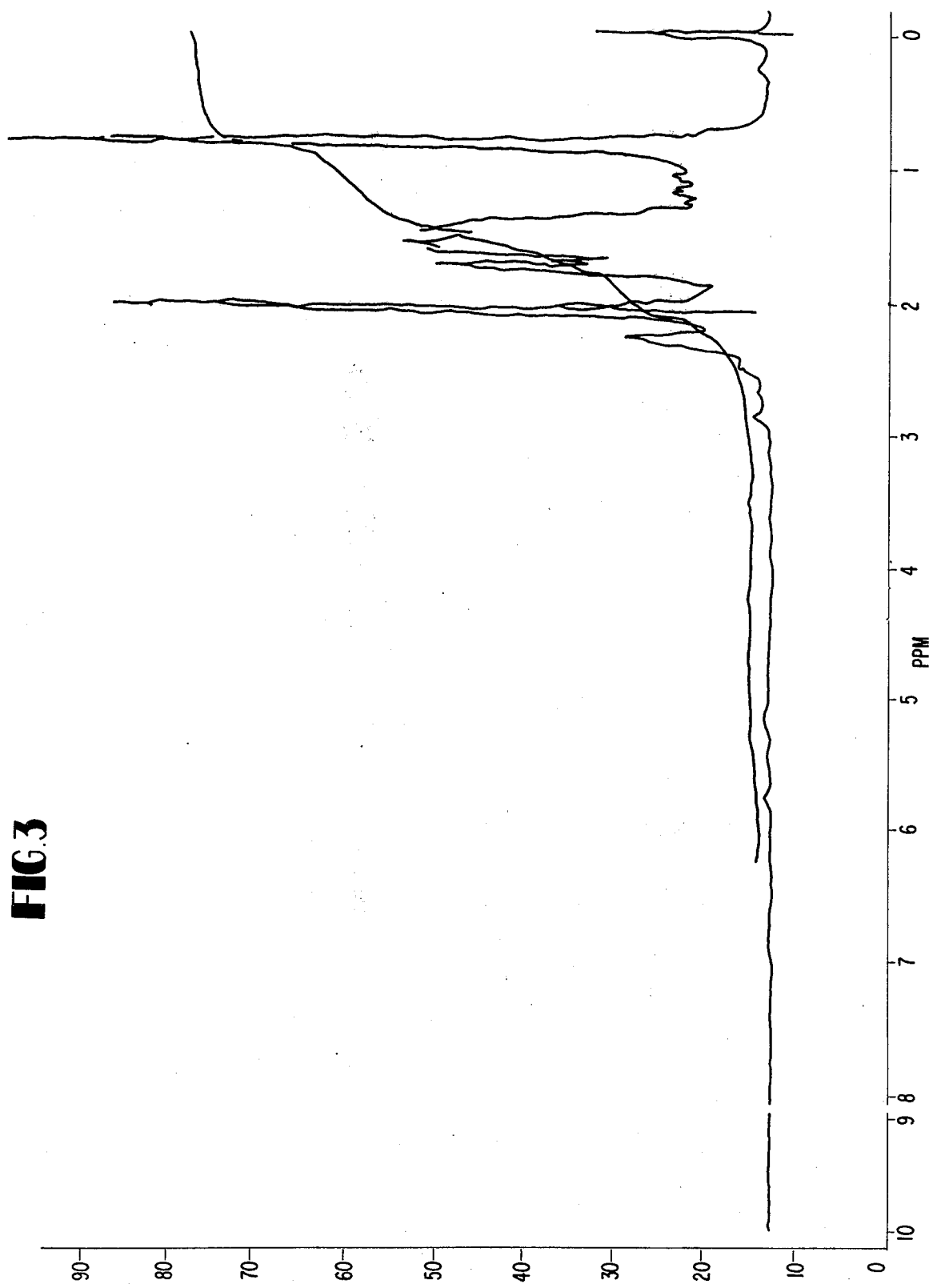
FIG. 3 is an NMR spectrum of Compound (I) obtained according to the present invention.

Compound (I) produced according to the present invention has the molecular formula, $C_{17}H_{26}O$, and a structure represented by the formula (I)

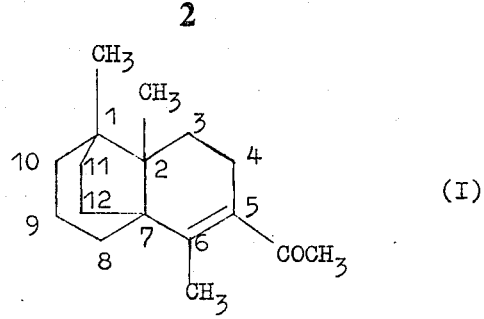

(I)

According to this invention, Compound (I) can be easily obtained much more clearly than conventional amber-like fragrant substances, and is also of industrial value because of its excellent amber-like fragrance.

In order to achieve the acetylation of Compound (II), for example, Compound (II) is reacted with an acetylating agent such as acetyl chloride or acetic anhydride 4with acetic anhydride being especially preferred in the presence of an acid catalyst. The acetylation can be carried out in the presence or absence of a solvent. The molar ratio of acetic anhydride is generally about 1.1 to 5 moles, preferably 4 moles of acetic anhydride per mole of Compound (II). A suitable amount of acetyl chloride also is generally about 1.1 to 5 moles of acetyl chloride per mole of Compound (II).

Examples of suitable solvents which can be used are preferably halogenated hydrocarbons such as carbon tetrachloride, chloroform, methylene chloride, etc., and other solvents, e.g., saturated hydrocarbons such as hexane octane, etc., ethers such as diethyl ether, dipropyl ether, etc., and the like can also be used. The amount of the solvent is not particularly limited, but the solvent is generally used in the range of about 50 to 300% by volume to the volume of Compound (II).

As the acid catalyst, a Friedel-Crafts acid catalyst is preferably employed, and suitable examples f Friedel-Crafts acid catalysts include boron trifluoride, stannic chloride, ferric chloride, zinc chloride, polyphosphoric acid or a mixture of polyphosphoric acid and phosphoric acid, etc. The acid catalyst which can be used can vary in the range of from about equimolar amount to 1 to 2 mole% to Compound (II). It is generally advantageous for a strong acid catalyst such as boron trifluoride to be used at a lower concentration, and for a weak acid catalyst such as zinc chloride to be used at a higher concentration.

The reaction is carried out at a temperature of about −5° to 100° C, preferably −5° to 85° C. In order to obtain the best results, the preferred reaction temperatures vary depending upon the kind of acid catalyst used. For example, when boron trifluoride is used, the reaction is preferably carried out at about 0° C in an ice bath, and when stannic chloride or ferric chloride is used, the reaction is preferably carried out at a temperature of about 10° to 50° C. Furthermore, when zinc chloride or polyphosphoric acid or a mixture of polyphosphoric acid and phosphoric acid is used, the preferred reaction temperature ranges from about 70° to 80° C.

The reaction time varies depending upon the kind of solvent, the amount of the solvent used and the reaction temperature, but is suitably about 30 minutes to 10 hours. The completion of the reaction can be detected by gas chromatographic analysis, and therefore, the reaction time can be determined by setting the operation conditions.

After completion of the reaction, the reaction solution is diluted with water, and the remaining acetylating agent is hydrolyzed, followed by extraction with a solvent such as n-hexane, etc. The extracted oily layer is washed with a basic solution, e.g., a dilute solution of a basic substance such as sodium carbonate, sodium bicarbonate, sodium acetate, etc., e.g., at a concentration of about 5% by weight, and the resulting acetic acid, the acid catalyst and the like are neutralized and removed. Thus, the extracted solution is concentrated and distilled under a reduced pressure to obtain Compound (I).

Compound (II) used as a starting material in the process of this invention can be prepared by subjecting 1,5,9-trimethylcyclododecatriene-1,5,9 (hereinafter "1,5,9-TMCDT") which is a cyclic trimer of isoprene to an intramolecular ring closure reaction with an acid catalyst as disclosed in copending U.S. patent application Ser. No. 537,004, filed Dec. 27, 1974 (corresponding to Japanese Patent Application Nos. 4207/1974 and 102646/1974) filed simultaneously herewith.

The thus obtained Compound (I) is a fragrant substance having a rich natural ambergris-like fragrance and a peculiar wood-like odor. When Compound (I) is absorbed on a filter paper and allowed to stand in a room at room temperature (e.g., about 20° to 30° C), the residual fragrance is found to be very strong and to last for over 1 week.

The utility value and application range of Compound (I) are wide as a perfumery material. That is, Compound (I) can be widely used as a perfume, for example, as a component for a rich perfume to a perfume for an inexpensive soap.

The present invention is further illustrated in greater detail by reference to the following Reference Example and Examples, but the examples are not to be construed as limiting the scope of this invention. Unless otherwise indicated, all parts, percents, ratios and the like are by weight.

REFERENCE EXAMPLE

Into a one liter three-necked flask were charged to 150 g of 1,5,9-trimethylcyclododecatriene-1,5,9 (1,5,9-TMCDT) having a melting point of 91° to 92° C, 260 ml of formic acid and 150 ml of dichloromethane, and these materials were mixed and maintained at a temperature of 5° to 10° C. A mixed solution of 7.5 ml of sulfuric acid and 40 ml of formic acid was then added dropwise thereto over a period of 30 minutes while keeping the temperature at 5° to 10° C. The resulting materials were reacted with stirring at that temperature for 3 hours, and further reacted with stirring at room temperature (i.e., about 20° to 30° C) for 3 additional hours. After completion of the reaction, dichloromethane was recovered by distillation, and formic acid was then distilled off under reduced pressure. The residue was neutralized and washed with a 3% aqueous sodium bicarbonate solution, and dried with anhydrous sodium sulfate, followed by distillation in vacuo, whereby 135 g of the fraction of Compound (II) having a boiling point of 75°–80° C/0.05 mmHg was obtained.

As a result of the Ir, NMR and MAS spectra of Compound (II) and also as a result of X-ray crystal structural analysis of a crystalline ketone compound derived from Compound (II), Compound (II) was determined to have the structural formula (II)

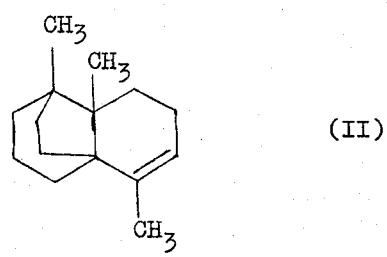

EXAMPLE 1

Into a 500 ml four-necked flask equipped with thermometer, a dropping funnel and a reflux condenser were charged 26 g (0.077 mol) of polyphosphoric acid ($H_6P_4O_{13}$) and 27.5 g of phosphoric acid, and these materials were maintained at a temperature of 75° to 80° C. 80 g (0.78 mol) of acetic anhydride was then added dropwise thereto over a period of 30 minutes. Subsequently, 41 g of (0.2 mol) of Compound (II) was added thereto over a period of 1.5 hours at that temperature, and these materials were stirred for 4 hours and cooled to room temperature (i.e., about 20° to 30° C). 200 ml of water was then added thereto and the contents were allowed to stand. After extraction with 200 ml of n-hexane, the extracted solution was washed successively with water, a 5% aqueous sodium bicarbonate solution and water, and dried with anhydrous sodium sulfate. Then, the n-hexane was recovered by distillation, and the residue was distilled under reduced pressure, whereby 42 g of an oily fraction having a boiling point of 110°–115° C/1.5 mmHg was obtained in a yield of 85%.

Refractive Index: $n_D^{25}$ 1.5253

| Elemental Analysis: | C | H |
| --- | --- | --- |
| Calculated (%): | 82.87 | 10.64 |
| Found (%): | 82.75 | 10.69 |

IR Spectrum:
  α,β-Unsaturated ketone characteristic absorption: 1682 cm$^{-1}$
MAS Spectrum: M$^+$ 246 (molecular ion)
NMR Spectrum:

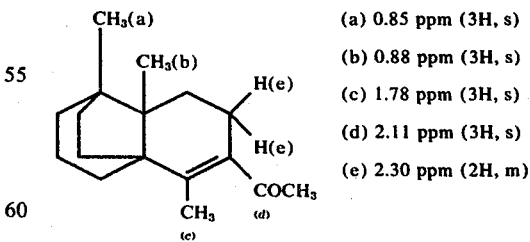

(a) 0.85 ppm (3H, s)
(b) 0.88 ppm (3H, s)
(c) 1.78 ppm (3H, s)
(d) 2.11 ppm (3H, s)
(e) 2.30 ppm (2H, m)

EXAMPLE 2

Into a 500 ml four-necked flask equipped with a thermometer, a dropping funnel, a reflux condenser and a stirrer were charged 100 g (0.49 mol) of Compound (II) and 100 g of methylene chloride, and 10 g of stannic chloride was added thereto over a period of one hour at a temperature of 25° to 30° C. 200 g (1.96 mols) of acetic anhydride was then added to the resulting mixture over a period of 2 hours at a temperature of 20° to 30° C, and the mixture was further reacted at a temperature of 22° to 28° C for 2 additional hours. The resulting mixture was then treated in the same manner as described in Example 1, whereby 92.5 g of Compound (I) was obtained in a yield of 77%.

EXAMPLE 3

Into a 500 ml four-necked flask equipped with a stirrer, a thermometer, a reflux condenser and a dropping funnel were charged 135 g of acetic anhydride and 155 ml of a 50% diethyl ether solution of a boron trifluoride-diethyl ether complex salt, and maintained at 0° C. 50 g of Compound (II) was then added thereto over a period of 2 hours at that temperature, and the contents were stirred for 2 hours at that temperature. Subsequently, the resulting mixture was poured into 400 g of ice and a 5% aqueous sodium hydroxide solution was then added thereto, followed by the same work-up procedures as described in Example 1. Thus, 42.5 g of Compound (I) was obtained in a yield of 71%.

EXAMPLE 4

The following formulation is suitable as a base for a perfume or an eau-de-cologne:

|  | g |
|---|---|
| Civet Absolute | 5 |
| Musk Absolute | 5 |
| Oak Moth Absolute | 30 |
| Vanilla Absolute | 10 |
| Musk Ambrette | 80 |
| Sandalwood Oil | 50 |
| Patchouli Oil | 80 |
| Methyl Ionone | 30 |
| Vetiver Oil | 80 |
| Eugenol | 20 |
| Phenylethyl Alcohol | 30 |
| Geraniol | 30 |
| Benzyl Acetate | 30 |
| Jasmine Absolute | 20 |
| Hexylcinnamic Aldehyde | 50 |
| Linalool | 50 |
| Linalyl Acetate | 50 |
| Bergamot Oil | 120 |
| Compound (I) | 80 |
|  | 850 g |

EXAMPLE 5

The following formulation is suitable as for a soap perfume:

|  | g |
|---|---|
| Ethylene Brassylate | 50 |
| Sandalwood Oil | 30 |
| Oak Moth Resinoid | 10 |
| Patchouli Oil | 30 |
| Coumarin | 40 |
| Bornyl Acetate | 30 |
| Citronellol | 80 |
| Tetrahydrogeraniol | 10 |
| Petigrain Oil | 15 |
| Lavandine Oil | 80 |
| Stearyl Acetate | 15 |
| Pineneedle Oil | 10 |
| Linalool | 170 |
| Linalyl Acetate | 130 |
| Compound (I) | 100 |
|  | 800 g |

While the invention has been described in detail and with reference to specific embodiments thereof, it will be apparent to one skilled in the art that various changes and modifications can be made therein without departing from the spirit and scope thereof.

What is claimed is:
1. A perfume composition containing 5-acetyl-1,2,6-trimethyltricyclo[5,3,2,0$^{2,7}$]dodeca-5-ene having the formula (I)

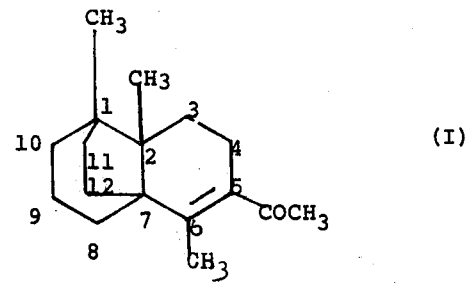

and other perfumery ingredients.

* * * * *